US012636330B2

(12) United States Patent
Di Maio

(10) Patent No.: US 12,636,330 B2
(45) Date of Patent: May 26, 2026

(54) COMPOSITION FOR THE TREATMENT OF SKIN AND MUCOUS MEMBRANE DISEASES

(71) Applicant: NEILOS S.R.L., Piano di Sorrento (IT)

(72) Inventor: Umberto Di Maio, Piano di Sorrento (IT)

(73) Assignee: NEILOS S.R.L., Piano di Sorrento (IT)

( * ) Notice: Subject to any disclaimer, the term of this patent is extended or adjusted under 35 U.S.C. 154(b) by 622 days.

(21) Appl. No.: 17/800,382

(22) PCT Filed: Feb. 12, 2021

(86) PCT No.: PCT/IB2021/051177
§ 371 (c)(1),
(2) Date: Aug. 17, 2022

(87) PCT Pub. No.: WO2021/165802
PCT Pub. Date: Aug. 26, 2021

(65) Prior Publication Data
US 2023/0085344 A1 Mar. 16, 2023

(30) Foreign Application Priority Data

Feb. 18, 2020 (IT) ........................ 102020000003221

(51) Int. Cl.
| | |
|---|---|
| *A61K 36/09* | (2006.01) |
| *A61K 9/00* | (2006.01) |
| *A61K 9/06* | (2006.01) |
| *A61K 31/728* | (2006.01) |
| *A61K 33/38* | (2006.01) |
| *A61P 17/02* | (2006.01) |

(52) U.S. Cl.
CPC ............ *A61K 36/09* (2013.01); *A61K 9/0034* (2013.01); *A61K 9/0043* (2013.01); *A61K 9/006* (2013.01); *A61K 9/06* (2013.01); *A61K 31/728* (2013.01); *A61K 33/38* (2013.01); *A61P 17/02* (2018.01)

(58) Field of Classification Search
None
See application file for complete search history.

(56) References Cited

FOREIGN PATENT DOCUMENTS

| | | | | | |
|---|---|---|---|---|---|
| EP | 3257516 A1 | * | 12/2017 | .......... | A61K 31/728 |
| WO | WO-2021165802 A1 | | 8/2021 | | |

OTHER PUBLICATIONS

Politano, A.D., et al., Use of Silver in the Prevention and Treatment of Infections: Silver Review, Surg. Infect., 14 (Feb. 1, 2013) pp. 8-20. (Year: 2013).*
Politano, A., et al., "Use of Silver in the Prevention and Treatment of Infections: Silver Review," Surg Infect (Larchmt) 14(1):8-20, Mary Ann Liebert, United States (Feb. 2013).
International Search Report and Written Opinion for International Application No. PCT/IB2021/051177, European Patent Office, Netherlands, mailed on Jun. 2, 2021, 10 pages.

* cited by examiner

*Primary Examiner* — Dominic Lazaro
(74) *Attorney, Agent, or Firm* — STERNE, KESSLER, GOLDSTEIN & FOX P.L.L.C.

(57) ABSTRACT

The present invention relates to a composition comprising as active ingredients an extract of *Cetraria islandica*, silver and/or a salt thereof and hyaluronic acid and/or a salt thereof. The present invention further relates to the use of such composition for the treatment of skin and/or mucous membrane diseases.

7 Claims, No Drawings

COMPOSITION FOR THE TREATMENT OF SKIN AND MUCOUS MEMBRANE DISEASES

FIELD OF THE INVENTION

The present invention relates to a composition comprising as active ingredients an extract of *Cetraria islandica*, silver and/or a salt thereof and hyaluronic acid and/or a salt thereof. The present invention further relates to the use of such composition for the treatment of skin and/or mucous membrane diseases for example due to microbial infections or inflammation and irritation.

STATE OF ART

The skin diseases can be classified following the present distinction:

Primitive elementary lesions

Secondary lesions

Pathognomonic lesions

Very simple lesions such as spot, macula, plaque, vesicula, blister, nodule, nodosity, erythema, wheal, pustule or cysts belong to the first group.

The second group includes squama, keratosis, crust, rhagade, excoriation, erosion, ulcer, scar.

The third group of lesions refers to more complex situations such as blackhead, scutolo, taleangiectasia.

Oral Cavity

The oral cavity is often seat of lesions or anatomic anomalies which could cause more or less unfounded concern and which appear mainly in non-specific way under the form of blisters, excrescences, whitish or red patches and erosions/ulcers. The cause of such lesions are pathologies which can be even very different and determined by distinct causes: by dental decay (bacterial infection in teeth) which can cause toothache with different entity to the formation of plaque and tartar (bacterial depositions), by gingivitis to periodontitis caused by aerobic and anaerobic germs to the lesions of mucous membranes of different nature (injuries and irritations due to prosthesis, formation of aphthae and ulcers on the mouth's tissues caused by Herpes and mycetes), by problems to joints of the jaw or other dysfunctions to craniofacial malformations (such as also cleft lip and fissured palate).

The infections supported by Herpes S. (herpetic stomatitis) appear as small vesicles having light colour and being painful, they are contagious and can relapse, usually, in conjunction with a lowering of immune defenses. In the serious cases and in immunocompromised people, the use of antiviral drugs by oral route can be required.

For aphthous stomatitis instead a local therapy with antiseptics and steroid drugs is indicated. It consists in the appearance of small single or multiple very painful superficial aphthae, having a diameter of 2-3 mm with yellowish white bottom and reddened outlines, which heal spontaneously within 10-15 days.

The most common mycotic infection is supported by *Candida* A. and typically affects the back of the tongue or the soft palate. The cause is a fall of the local and general defensive powers of the organism or a poor hygiene. It affects especially infants and older people (above all bearers of removable prostheses) and it responds to treatments with antimycotics.

In most cases, such pathologies are benign conditions, of traumatic or infective origin, but in some cases the same lesions can be the signs of systemic problems (some of autoimmune origin, such as pemphigus and lichen planus, and others of considerable social importance, such as syphilis and AIDS), which require a specialized treatment, based upon antivirals or antibiotics, and sometimes the first step of pathologies with malign evolution, such as oropharyngeal cancer. This is the rational therefor the current Guidelines impose not to neglect and above all not to underestimate these lesions, which once intercepted at an early stage can make the difference in short- and long-term prognosis.

It is important to underline that, as OMS and CDC do, the fact of having a good oral hygiene is a condition which strongly influences the whole health state and well-being of the person and which can have even very heavy effects on the daily life of the individuals. Behind this, to say the truth, there are a series of preventive practices. Among the main causes of the mouth problems, in fact, there are poor hygiene and poor nutrition which favour the development of dental decays, tartar and lesions of the oral cavity.

Nasal Cavities

A variety of pathologies, instead, affect the nose and sinuses, whether they are inflammatory, infective or tumoral. Due to its prominent position, the nose, first of all, is particularly vulnerable to trauma, fractures included. The nose mucous membrane can inflame, by originating rhinitis, which can propagate to the coating of the sinuses, causing rhinosinusitis. In rhinitis, the phlogistic process, having acute or chronic course, is the consequence of bacterial (S. *Pneumoniae*, H. *Influenzae*, S. *Aureus* and M. *Catarrhalis* are only some of them), viral (adenovirus for the common cold and human parainfluenza viruses, for example) or irritating insults. The first symptom generally is rhinorrhea: the inflammation causes an excessive production of mucus, thereto nasal congestion and variable symptoms are associated, depending upon aetiology (itch, sneezing, anosmia, light headache and feeling of tiredness). The diagnosis is generally clinical, whereas the treatment includes humidification of the surrounding air, nasal vasoconstrictors and sometimes ingestion of simple analgesics and antipyretics. There are no antiviral drugs effective for the common cold, but a bacterial superinfection can require an appropriate antibiotic treatment. The nasal washing with the simple physiological solution in pre-packed products or in the syringe without needle represents a fundamental local hygienical-preventive measure.

The onset of nasal pathologies varies mainly based upon age: children tend to have more easily rhinitis of infective, viral or bacterial origin, due to an immune system which is still immature and does not succeed in contrasting effectively the pathogen agents therewith they come into contact early, especially in school environments. Over the years then, above all in predisposed subjects, more and more frequent allergies follow, which hinder night rest and compromise the life quality. The causes of allergic rhinitis generally are pollen, mildew, powders, animal hair and other substances, called allergens, which in predisposed patients trigger an excessive production of IgE, particular antibodies responsible for the reaction. The most common symptoms are nasal obstruction, dripping, itch and sneezing, which in the most serious forms can be accompanied even by headache, eye disorders, loss of smell and taste. However, they are symptoms reversible spontaneously with the suspension of the exposition to the allergen, or after a vaccine or pharmacological therapy (decongestants, antihistamines and corticosteroids). Vasomotor rhinitis, instead, are little known but very widespread—often labelled as non-specific or idiopathic—which have the same symptoms of the allergenic ones, but result to be negative to the traditional prick-tests. The pathogenesis is not clear but it seems to involve neurogenic inflammation mechanisms: since they do not derive from allergens, they have no seasonality but tend to be chronic, predisposing in time to complications, such as asthma or nasal polyposis. Different antihistamine agents, thereamong azelastine, if applied locally, can result to be useful and effective.

Ear Cavity

Even an ear at first perfectly healthy is subjected to diseases of various type. The main threat to its integrity is represented by pathogen germs which can cause otitis and other more or less serious infections. Since the ears are useful not only to hear, but even are the organs responsible for equilibrium, some specific pathologies can damage this very important "sense".

Caused by bacteria or viruses, but even by the accumulation of water in the ear canal (in case of summer otitis), otitis can be more or less problematic depending upon the fact they limit to affect the external ear, or the middle or internal one. Children are particularly subjected thereto. Continuous purulent malodorous secretions (otorrhea), pain and inflammation constitute the main symptoms, but usually even hearing loss (hypoacusis) and fever are quite common. If otitis has no complications, the treatment consists in ingesting anti-inflammatory drugs and in applying possibly local medicaments to restore the ear equilibrium conditions. In case of bacterial infections, the antibiotic treatment is necessary. An infection of the middle ear (otitis media), moreover, is the most common not traumatic cause of tympanic perforation, thereto generally sudden ear pain (earache) is associated, sometimes followed by ear bleeding, hearing loss and perception of noises in the ear. Physicians can note perforation with an otoscope and, generally, the eardrum heals on itself. Sometimes, however, it is necessary to have recourse to surgical repair.

Among the symptoms of cholesteatomatous otitis media, chronical pathology characterized by a hyperproduction of epithelial cells inside the middle ear, there are then otorrhea, pain and progressive hearing loss (hypoacusis). Cholesteatoma is treated with antibiotics only when it is in mild form or taken at the beginning thereof. Differently, the solution is represented by the surgical removal of excess tissues. At last, there is presbycusis, a gradual, progressive and inevitably hearing loss which happens in many elderly subjects, above all after the age of 65. Since the cause is aging, it is not possible to prevent the process, however, it is possible to make up for the hearing loss by having recourse to the removable prostheses (the classical hearing aids), or permanent bone prostheses.

Genital Apparatus

Studied in symptomatic key, several genital infections are characterized by similar, often mistakable symptoms: for this reason, the recognition of the pathogen involved in the disease is not always so immediate. Apart from the generality of prodromes, sometimes, even the difficulty, by the same patient, in identifying certainly the precise painful anatomical genital seat is added, by making the diagnosis clearly more complex. The medical examination with the differential diagnosis is the only effective method to ascertain the infection and establish the seriousness level thereof.

The clinical history of the patient, then anamnesis, gives a general idea of the subject's health state, on the possible alterations of the endocrine equilibrium, on the effectiveness of the autoimmune system and on all previous pathologies. The diseases affecting genitals are several: some involve the remaining skin and occasionally they can localize even at the level of the genitals (they are the common dermatological diseases), whereas others appear exclusively at the level of the genitals (such as urethritis), but later they can even spread to other body portions (such as for example syphilis or the contagious mollusc). The genital infections area expression of a bacterial, viral or fungus insult which, often, is favoured by the sexual contact with carrier patients or poor hygienic conditions. However, improper diet, sedentary lifestyle and administration of some drugs are not to be excluded as possible causes. Vulvovaginitis and vaginosis are inflammations which can determine symptoms like vaginal discharges, intimate itching, but even pain. Vaginosis, in particular, reflects a radical alteration of the vaginal ecosystem with a quantitative subversion of the existing microbial species: lactobacilli are considerably reduced or absent, whereas, in higher concentrations than normal, bacteria such as *Gardnerella* V. and other obliged anaerobes predominate. In some cases, the abnormal growth of the pathogen is associated to the appearance of abundant greyish-white and distinctly malodorous secretions. In such case, the recourse to metronidazole and, together with it or replacing it, the recourse to topic therapies is the first choice. Then lavages or gels will be used, at the end of sexual intercourses and after the end of the menstrual flow, the main purpose thereof is to reconstitute the normal vaginal flora. HIV/AIDS, human papillomavirus (HPV), genital herpes and vaginal trichomoniasis, instead, are sexually transmissible diseases which can involve vagina; in order to avoid their transmission, the health institutions recommend safe sex practices (barrier methods).

*Candida* A. fungus constitutes 20-30% of all female and male genital infections. Balanoposthitis for example, an infection of the gland head often extended to prepuce in man, is frequently supported indeed by this mycete. Most infections due to *Candida* can be treated and lead to minimum complications, such as redness, itch and annoyance, if treated with an adequate antimycotic.

Proctology

The pathologies involving the anorectal region are several; the most frequent ones are haemorrhoids, anal fissures, anal fistulas, abscesses and all neoplasms of anus, rectum and colon. Such conditions, even when they are benign (and this is most of the time), are often strongly disabling due to pain or other symptoms affecting the life quality. For a correct diagnosis of these pathologies often a proctological medical examination through rectal examination and/or anoscopy is sufficient. In the most complex cases one avails of second-level diagnostics. Haemorrhoids are absolutely the most frequent anal pathology. They are veins which increase in volume inside the anal channel, encountering congestion and inflammation phenomena. They can generate anal pain, especially during defecation, emission of red blood, itch, protrusion outside, until prolapse.

In most cases, when the disease is diagnosed and treated early, the proctologist is capable of solving the problem with pharmacological medical therapy, generally by means of drugs with topical use, and correction of some lifestyle habits, above all food habits, or with absolutely painless ambulatory methods. The anal fissure instead is a fissuring of the mucous membrane inside the anal canal, more often localized on the rear wall, extremely painful upon the passage of faeces and which can cause bleeding. After haemorrhoids and fissures surely abscesses and fistulae are third in the frequency order. Such affections, strictly connected therebetween and often associated, are pathologies deriving from inflammatory processes against peri-anal glands.

In the light of what said, there is still the need for solutions for the treatment of skin and/or mucous membrane diseases for example due to microbial infections or to inflammation and irritation.

SUMMARY OF THE INVENTION

The present invention is based upon the search for and identification of a combination of substances which, when used in association, exert an effective and enhanced action in treating the diseases of the skin and/or mucous membranes of various origin.

From the performed experimentation, the inventors have found that the association of an extract of *Cetraria islandica*, silver and/or a salt thereof, hyaluronic acid and/or a salt thereof is particularly effective.

The present invention further relates to compositions, comprising the above-mentioned association and at least one or more excipients. The present invention further relates to a kit of portions including the above-mentioned active principles separated and formulated in suitable oral dosage form for sequential or contemporary administration of the different active principles.

The present invention further relates to the use of said associations, compositions and kits in the treatment of skin and/or mucous membrane diseases, in particular in the treatment of irritation and/or disease of the mucous membranes, of bacterial as well as fungus nature, for example associated to pathological states and to a weakening of the immune defenses.

The present invention allows to obtain at the same time an antimicrobial effect, an anti-inflammatory effect and an antioxidant effect. Thanks to the three active principles, the present association constitutes a valid help for the anti-bacterial action, exerted: by Ag+ ion through the irreversible damage of the enzymatic system situated in the membrane of several pathogens;

from the aromatic acids included in the lichene islandico, in particular usnic acid, interfering with the capability of intercellular communication (essential for the formation of the bacterial biofilm), by inhibiting the quorum-sensing (process of recognition between bacteria assigned to chemical signals); by the hyaluronic acid which has revealed a bacteriostatic activity on some bacterial strains. Thanks to the lichenin contained in the extract of *Cetraria Islandica*, capable of forming protective mucilage of the mucous membranes, and to the combined properties of hyaluronic acid and silver, the anti-inflammatory activity of the composition is strengthened, which is expressed in the recruitment of lymphocytes T-helper (mediated by the link between hyaluronic acid and receptors CD44) and in the down-regulation of the mast cell degranulation (mediated by the silver), thus relieving the painful symptomology associated to such phlogistic processes and speeding up the healing process (above all in wounds). The antifungal activity exerted by the three active ingredients on the infections caused by candida, responsible for local inflammations and discomfort sensations in many people, is not less important. Moreover, some researchers have supposed, having found the presence of candida in mucus of several patients, that its presence in the nasal cavity causes an immune response, by causing in this way irritation and inflammation. Moreover, the fungal infections are also the most common cause of the appearance of aphthae in the buccal cavity and of pathologies in the genital field (vaginal candidiasis). The anti-fungal activity and, in addition, the antioxidant one carried out by the three active ingredients represent an added value to the above-described activities attributed to the association, which are well suited to a local and routine use. Other advantages and features of the present invention will result evident from the following detailed description.

GLOSSARY

The terms used in the present description are as generally understood by the person skilled in the art, except where otherwise indicated.

Under the term "extract", in the context of the present description, any product is meant attributable to a plant drug including all products deriving from mechanical treatments (pulverization, trituration, mixing and/or other methods) or by extractive treatments (extraction with solvent, distillation and/or other specific methods) carried out on a drug.

DETAILED DESCRIPTION OF THE INVENTION

As above mentioned, the present invention relates to an association comprising as main active principles at least an extract of *Cetraria islandica*, silver and/or a salt thereof and hyaluronic acid and/or a salt thereof.

The main active ingredients of the association of the invention are described hereinafter.

Silver

The academic medicine has known and has used for some time silver, under the form of salts or nanoparticles (AgNps), which had and still have a therapeutic utility thereof, mainly linked to the organism defence from infections and diseases mediated by bacteria, viruses and mycosis. The effectiveness of the silver compounds is based upon the capability of biologically active Ag+ ion to damage irreversibly the key system of the enzymes in the membrane of the pathogens. In the herein described compositions and kits, Ag+ ion or Salts thereof, colloidal silver, nanoparticle silver, citrated silver, complexed silver could then be used.

Extract of *Cetraria Islandica*

Under the wording "at least an extract of *Cetraria islandica*" in the context of the present description it is meant that the composition can include an extract of lichen belonging to the species *Cetraria islandica* or Lichene islandico. The extract could be prepared according to the procedures known in the state of art, for example, it could be a dry extract, or prepared by means of extraction in water or in alcohol solution, and optionally lyophilized. Preferably an extract of *Cetraria islandica*, with ratio extract/drug 1 to 4 obtained from the thallus will be used.

The person skilled in the art could adapt the amount of extract used in the preparation of the formulations to be administered depending upon needs. The doctor could be able to identify the optimum dosage for the subject to be treated based upon age, sex, weight and general health status. Then, the dosage of the single active principles can be adapted, even during the period of ingesting the association or composition of the invention depending upon the results obtained in time.

Hyaluronic Acid

The hyaluronic acid (HA) also known for its re-epithelizing action is one of the active ingredients of the composition of the present invention, wherein even the Salts thereof, such for example sodium hyaluronate, could be used. The hyaluronic acid could be for example in form of gel or solution, with low or high molecular weight.

The term hyaluronic acid with high molecular weight in the present document describes a hyaluronic acid having a molecular comprised between 1.0 million Daltons at about 4.0 MDa. For example, the high molecular weight of hyaluronic acid could have a molecular weight of about 1.0 MDa. In another example, it can have a molecular weight of about 2.8 MDa. The term hyaluronic acid with low molecular weight in the present document describes a hyaluronic acid having a lower molecular weight at about 1.0 MDa. Hyaluronic acid with low molecular weight can have a molecular weight comprised between about 200,000 Da (0.2 MDA) to less of about 1.0 MDa, for example, between about 300,000 Da (0.3 M Da) to about 750,000 Da (0.75 MDA). The conjugated hyaluronic acid for example could have a viscosity between 50,000 and 300,000 mPa.

The inventors have detected the optimal pro-dose dosages (or per single dosage unit) of each substance of the association to obtain synergic therapeutic effects.

In particular there are the best effects when the extract of *Cetraria islandica* is present in an amount between 0.01% and 30%, preferably between 0.05% and 15%, still more preferably between 0.1% and 10%; the silver and/or a salt thereof is present in an amount between 0.0001% and 20%, preferably between 0.0005% and 10%, still more preferably between 0.0006% and 5% and hyaluronic acid and/or a salt thereof is present in an amount between 0.005% and 30%, preferably between 0.01% and 20%, still more preferably between 0.05% and 10% with respect to the total weight of the final pharmaceutical form including all excipients.

The present invention further relates to compositions comprising the association according to any one of the herein described embodiments and one or more suitable excipients.

The composition can include other components, such as for example excipients, carriers, stabilizers, preservatives and the like and/or other active principles.

The compositions according to any one of the embodiments provided in the present description can be formulated in any form and by any administration route and associated to any other component, in a variety of ways.

According to a preferred embodiment, the compositions of the invention are compositions for topical use, for example for nasal, buccal, vaginal, genital, anal, auricular, cutaneous application.

The compositions will be for example in solid, liquid or gel form, for example, cream, powder, solution, suspension, ointment, gel, spray.

Suitable excipients can be selected among those usually known in the state of art and include, but they are not limited thereto: diluents, lubricants (for example magnesium stearate, stearic acid, waxes), dispersants, surfactants (for example sodium lauryl sulphate and polysorbates), flavouring agents, adsorbents (for example silica gel, talcum, starch, bentonite, kaolin), glidants and anti-adherent agents (for example talcum, colloidal silica, corn starch, silicon dioxide), dyes (for example iron oxides), opacifiers (for example titanium oxide), antioxidants, binders (for example rubbers, starch, gelatine, cellulose derivatives, sucrose, sodium alginate), disaggregating agents (starch, microcrystalline cellulose, alginic acid, crospovidone), plasticizers (for example ethylcellulose and other cellulose derivatives, acrylates and methacrylates, glycerol and sorbitol), preservatives (for example parabens, sulphur dioxide), viscosifying agents, emulsifiers, humectants, wetting agents, chelating agents and mixtures thereof.

The compositions of the present invention, for example, will be a medical device, a cosmetic, a dietary supplement, a nutraceutical, dietetic or nutritional composition, a food product, a beverage, food, a nutraceutical, medicated food, food for special medical purposes or a pharmaceutical composition.

The compositions according to any one of the herein described embodiments could be used both by the human beings and by animals.

The combination of the above-mentioned active principles could be used formulated in one single composition according to the various above-described embodiments or in a kit including the different separate ingredients, for example, in single compositions formulated in suitable oral dosage form as defined above for the sequential or contemporary administration of the different active principles.

Therefore, the present invention further relates a kit of portions which include the different active principles of the association according to any one of the herein described embodiments separated and formulated in suitable form of oral dosage for the sequential or contemporary administration of the different active principles.

The action of the single components and of the association set forth by the present invention was evaluated by means of in vitro and/or in vivo tests which, besides, highlighted that the composition of the invention is particularly effective thanks to the (synergic) potentiation action of its components.

Therefore, the present invention further relates to the association, to the compositions and to the kit, according to any one of the herein described embodiments, for use in the treatment of microbial infections, for example for infections of S. *Aureus*, L. *Monocytogenes; Salmonella* T., *Shigella* S., *E. Coli* and P. *Aeruginosa, Candida*. In particular in the treatment of the irritation and/or disease of the mucous membranes, caused by microbial infections of bacterial or fungus nature, for example associated to pathological states and to a weakening of the immune defenses. The association of the above-mentioned active principles could be formulated in one single composition or in a kit according to the various above-described embodiments and prepared for example by mixing the active principles selected with possible other excipients as it is known to the person skilled in the art.

EXAMPLES

Hereinafter some not limitative examples of the compositions according to the present invention are reported. In the examples the percentages, if present, are to be meant as percentages by weight. Modifications or variations of the herein exemplified embodiments, obvious to a person skilled in the art, are comprised in the enclosed claims. Where it is not specified, the remaining part of the composition are excipients Example 1

| Active principle | % in composition |
| --- | --- |
| Cetraria islandica | 0.5 |
| Silver | 0.06 |
| Hyaluronic acid sodium salt | 0.1 |

Pharmaceutical form: spray for nasal application

Example 2

| Active principle | % in composition |
| --- | --- |
| Cetraria islandica | 0.1 |
| Silver | 0.005 |
| Hyaluronic acid sodium salt | 0.2 |

Pharmaceutical form: spray for buccal application

Example 3

| Active principle | % in composition |
| --- | --- |
| Cetraria islandica | 0.5 |
| Silver | 0.06 |
| Hyaluronic acid sodium salt | 0.05 |

Pharmaceutical form: spray for ear application

Example 3

| Active principle | % in composition |
| --- | --- |
| Cetraria islandica | 0.1 |
| Silver | 0.0006 |
| Hyaluronic acid sodium salt | 0.01 |

Pharmaceutical form: spray for cutaneous application

Example 4

| Active principle | % in composition |
| --- | --- |
| Cetraria islandica | 0.5 |
| Silver | 0.06 |
| Hyaluronic acid sodium salt | 0.1 |

Pharmaceutical form: cream for nasal application

Example 5

| Active principle | % in composition |
| --- | --- |
| Cetraria islandica | 0.05 |
| Silver | 0.0006 |
| Hyaluronic acid sodium salt | 0.01 |

Pharmaceutical form: cream for vaginal application

Experimental Evidence

The effectiveness of the association of *Cetraria islandica*, silver and/or a salt thereof and hyaluronic acid was evaluated according to known experimental models. In particular, for evaluating the different activities of the composition of the three active ingredients, in vitro and/or in vivo assays, known to the scientific literature, can be used. In order to demonstrate the antimicrobial effectiveness of the association, of particular interest for the prevention and/or the treatment of bacterial pathologies and surface mycosis, for example, in vitro assays on plate according to the method by spreading (Kirby-Bauer test, or methods of the small disks) or by micro-dilution result to be suitable, but even by means of MBEC Assay designated to quantify the biofilm. The bacterial strains in exponential growth phase selected for the study could be for example: S. *Aureus* and L. *Monocytogenes* such as Gram+; *Salmonella* T., *Shigella* S., *E. Coli* and P. *Aeruginosa* such as Gram−; at last, as fungus strain *Candida* A or others considered relevant for the purpose of the composition set forth by the present invention.

The synergic activity of the composition set forth by the present invention can be evaluated even through evaluation of MIC and MBC on bacterial or fungus strains.

The synergic effect obtained by using the three active ingredients in association can be highlighted by testing the association for its antimicrobial effect on male mice (n=60; 20 to 30 g) thereto, after anaesthesia, wounds with full cutaneous thickness on the back were performed and therethrough a certain bacterium (for example S. *aureus*) was inoculated. The rats were divided into groups, including control group. On established days (for example 0, 7, 14 and 21 of the experiment) photos were taken. Based upon the group, the control group, each active ingredient singularly and then even the mixture of the three ingredients of interest for the present composition were applied on the wound on day 0, to evaluate the way in which the association of silver, hyaluronic acid and lichene islandico speeds-up significantly the healing process of infected wounds. On the contrary, to demonstrate the anti-inflammatory effectiveness of the composition, of particular interest for the prevention and/or treatment of symptoms associated to phlogistic processes, in vitro assays result to be suitable which evaluate the capability of inhibiting the release of pro-inflammatory cytokines such as for example 1L-1, IL-5 and TNF-α and histamine and of inducing the one of anti-inflammatory cytokines such as IL-10, as well as of inhibiting the expression of enzymes such as 5-lipoxygenase and COX-2/PGE2 induced by IL-1 in primary cultures of human cells (for example mononuclear cells of the peripheral blood, such as monocytes and lymphocytes and on fibroblasts or other types of cells) and on pig leukocytes or other type of cell known to the person skilled in the art by means of ELISA test, Western Blotting or flow cytometry. By means of an in vivo model, instead, it was possible to test the association for its anti-inflammatory effect on BALB/C mice (female), to the ear thereof allergic dermatitis by contact was induced by means of inoculation of dinitrofluorobenzene (DNF). The topical treatment was performed once a day for 4 days and provided (for example for groups of about 15-30 mice): the control, each active ingredient singularly and then even the mixture of the three ingredients of interest for the present composition. The swelling and erythema to the ear were evaluated day by day. After 4 days of treatment, the mice were sacrificed and the ear of each one of them was removed for the histological and immunohistochemical examinations, TUNEL Assay and extraction of total RNA for RT-PCR examination. In the immunohistochemical examination the expression of cytokines was evaluated, the extraction of RNA was used to test the levels of the genes of interest involved in the various inflammatory reactions. At last, in order to demonstrate the antioxidant effectiveness of the composition, of particular interest for the prevention and/or treatment of symptoms associated to situations of stress in the organism, after physical damages, in vitro assays result to be suitable such as biochemical analyses on serum and spectrophotometric techniques, which evaluate the capability of incrementing the activity of GPX (Glutathione peroxidase) and of CAT (catalase), the active enzymes against the oxidative damage of the molecules inside the organism.

The invention claimed is:

1. A composition comprising as the active ingredients: (i) an extract of *Cetraria islandica* in an amount between 0.01% and 30% w/w, (ii) silver and/or a salt thereof in an amount between 0.0001% and 20% w/w; and (iii) hyaluronic acid and/or a salt thereof in an amount between 0.005% and 30% w/w.

2. The composition of claim 1, wherein said composition further comprises one or more excipients.

3. The composition according to claim 2 for topical use, in particular for nasal, vaginal, anal, auricular, cutaneous or buccal administration.

4. The composition according to claim 2 in a form selected from cream, powder, solution, suspension, ointment, gel, and spray.

5. A method of treating skin and/or mucous membrane diseases comprising administering the composition of claim 2 to a subject in need thereof.

6. The method of claim 5, wherein the composition is administered to oral mucus membranes, nasal mucus membranes, anal mucus membranes, auricular mucus membranes, genital mucus membranes and/or vaginal mucous membranes.

7. A method of treating microbial infections of the skin and/or mucous membranes comprising administering the composition of claim 2 to a subject in need thereof.

* * * * *